United States Patent [19]

Sikorski et al.

[11] Patent Number: 4,601,744

[45] Date of Patent: Jul. 22, 1986

[54] ESTERS OF N,N'-METHYLENE-BIS-[N-[(DIARYLOXY-PHOSPHINYL)METHYL]GLYCINE] AS HERBICIDES

[75] Inventors: James A. Sikorski, Kirkwood; Deborah Mischke, Creve Coeur; Gerard A. Dutra, Ladue, all of Mo.

[73] Assignee: Monsanto Company, St. Louis, Mo.

[21] Appl. No.: 698,484

[22] Filed: Feb. 5, 1985

[51] Int. Cl.[4] .......................... A01N 57/06; C07F 9/40
[52] U.S. Cl. ........................................ 671/86; 558/158
[58] Field of Search .............................. 260/932; 71/86

[56] References Cited

U.S. PATENT DOCUMENTS 4,067,719  1/1978  Dutra .................................... 71/86
4,089,671  5/1978  Dutra .................................... 71/86
4,120,689  10/1978  Dutra .................................. 71/86

*Primary Examiner*—Anton H. Sutto
*Attorney, Agent, or Firm*—David Bennett; Paul D. Matukaitis; Arnold H. Cole

[57] ABSTRACT

This invention relates to novel esters of N,N'-methylene-bis-[N-[(diaryloxyphosphinyl)methyl]glycine] which are useful as herbicides. The invention also relates to herbicidal methods and compositions employing the novel esters.

15 Claims, No Drawings

ESTERS OF N,N'-METHYLENE-BIS-[N-[(DIARYLOXYPHOSPHINYL)METHYL]GLYCINE] AS HERBICIDES

This invention relates to ester derivatives of N,N'-methylene-bis-[N-[(diaryloxyphosphinyl)methyl]glycine] which represent a new class of organic chemical compounds. This invention further relates to herbicidal compositions containing such derivatives and to herbicidal methods employing such compounds and compositions.

BACKGROUND OF THE INVENTION

U.S. Pat. No. 3,799,758 issued to John E. Franz on Mar. 26, 1974 describes the preparation and herbicidal utility of N-phosphonomethylglycine and its esters, amides, and salts.

U.S. Pat. No. 4,120,689 issued to Gerard A. Dutra on Oct. 17, 1978 describes alkyl-[di-(benzyl) or di-(aryl)] esters of N-phosphonomethylglycine which are produced by the reaction of a dibenzyl or diaryl phosphite with an N-methylene alkyl glycinate trimer. These esters and the hydrolysis products thereof containing at least one benzyloxy or aryloxy group bonded to phosphorus are compounds disclosed as having the Formula I

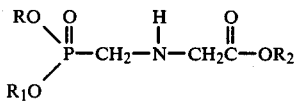

wherein

Re is a member of the group consisting of phenyl, benzyl, naphtyl, biphenyl, and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro or halo;

$R_1$ is hydrogen or an R group; and $R_2$ is a lower alkyl group or hydrogen, and the strong acid salts of the compounds wherein neither $R_1$ or $R_2$ is H. These compounds are useful as postemergent herbicides.

U.S. Pat. No. 4,067,719 issued to Gerard A. Dutra on Jan. 10, 1978, discloses esters of N-phosphonomethylglycinonitriles which are produced by the reaction of a diaryl phosphite with an N-methylene glycinonitrile trimer. These compounds and the hydrolysis products thereof are disclosed as having the Formula II

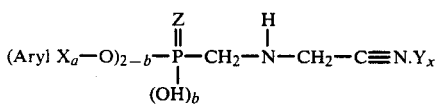

wherein (Aryl) is selected from phenyl, naphthyl, or biphenyl;

each X is a substituent on said Aryl selected from halogen, alkyl of 1 to 4 carbon alkoxy and alkylthio of 1 to 3 carbons, alkoxycarbonyl of 2 to 3 carbon atoms, methylenedioxy, cyano, trifluoromethyl, or nitro;

Z is oxygen or sulfur;

a is an integer from zero to 3;

b is an integer from zero to 1;

Y is a strong acid capable of forming a salt with the amino group; and x is zero or 2, provided that x must be zero when b is 1, as well as a process for producing such compounds. These N-phosphonomethylglycinonitriles are said to be useful as herbicides.

U.S. Pat. No. 4,089,671 issued to Gerard A. Dutra on May 16, 1978 describes N,N'-methylene-bis-[O,O-diaryl-N-phosphonomethylglycinonitriles] which can be produced concurrently with compounds of Formula II by the reaction of a diarylphosphite with an N-methylene-glycinonitrile trimer or sequentially from compounds of Formula II. These aminal derivatives are disclosed as having the Formula III

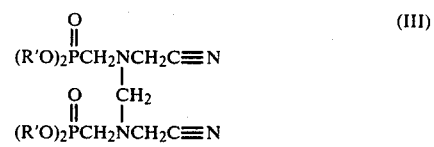

wherein

R' is a member of the group consisting of phenyl or naphthyl and phenyl or naphthyl substituted with 1 or 2 groups selected from the class consisting of halogen, lower alkyl, lower alkoxy, and lower alkylthio. These animal derivatives of N-phosphonomethylglycinonitrile are useful as post-emergent herbicides.

BRIEF SUMMARY OF THE INVENTION

In accordance with the present invention, there is provided novel ester derivatives of N,N'-methylene-bis-[N-[(diaryloxyphosphinyl)methyl]glycine] which represent a new class of organic chemical compounds and are represented by Formula IV

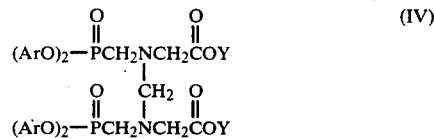

wherein

Ar is a member of the group consisting of phenyl or phenyl substituted with 1 or 2 groups independently selected from the class consisting of halogen, lower alkyl, and lower alkoxy; and Y is lower alkyl or aralower alkyl. These compounds are useful as post-emergent herbicides.

DETAILED DESCRIPTION OF THE INVENTION

The compounds of this invention are prepared by reacting a hexahydrotriazine derivative of the Formula V

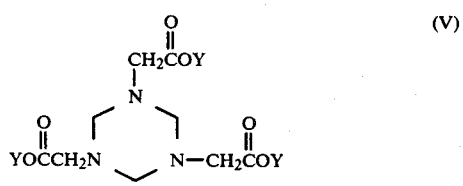

also illustrated as an N-methylene alkylglycinate trimer, [CH$_2$=NCH$_2$CO$_2$Y]$_3$, wherein Y is as defined above, with a diaryl phosphite of the Formula VI

 (VI)

wherein Ar is as defined above in an aprotic solvent which is inert with all of the reactants and products. The solution is maintained at a temperature sufficient to produce the aminal derivatives of Formula IV along with the corresponding compound of Formula I.

Such aminal derivatives of Formula IV have not been previously observed, detected, separated, or purified from the reaction mixture that produces compounds of Formula I. The compounds of this invention were not previously observed because analytical means capable of distinguishing them were not commonly available. By employing more recently available high-field $^{31}$P NMR spectroscopy, it is possible to observe and readily distinguish previously unknown compounds of Formula IV from the known compounds of Formula I in solution. However, all attempts to separate and purify compounds of Formula IV from such mixtures using either the crystallization techniques or the conventional low or medium pressure column chromatography methods described in the prior art, such as in Dutra, U.S. Pat. No. 4,089,671, failed to produce any pure aminal material. Instead, preparative thin layer chromatography (TLC) employing the recently developed Harrison Research Chromatotron (Model 7924) instrument allowed for the isolation of analytically pure samples of compounds of Formula IV, essentially free of any contamination by compounds of Formula I. Thus, the combined use of high-field $^{31}$P NMR spectroscopy and preparative TLC led to the first successful synthesis and isolation of compounds of Formula IV.

The temperature at which the reaction of compounds of Formula V with compounds of Formula VI is conducted is not critical. The temperature should be that which is sufficiently elevated so as to initiate and maintain this reaction. A temperature in the range of from about $-20°$ C. to about 200° C. can be employed. Generally it is preferred to employ a temperature in the range of about $+10°$ C. to about $+50°$ C., although greater or lower temperatures may be employed if desired.

In conducting the reaction of this invention, the ratio of reactants is not narrowly critical. It is apparent from the stoichiometry of the reaction that for best results in yield, it is preferred to employ ratios of the phosphite diester to trimer of at least 3 to 1. However, to facilitate isolation, one should employ a slight excess of the trimer over the required amount to insure complete consumption of the phosphite.

Due to the reactive nature of the various reaction intermediates and products, aprotic solvents should be employed which are inert to the trimer and the phosphite. It is also necessary that this reaction be conducted under essentially anhydrous conditions in order to prevent premature hydrolysis of the aminal products. For convenience and economy, it is preferred to conduct this reaction at atmospheric pressure.

Examples of acceptable aprotic solvents are acetonitrile, benzene, toluene, xylene, mono and dichlorobenzene, methylene chloride, chloroform, carbon tetrachloride, ethyl acetate, dimethylformamide, tetrahydrofuran, diethyl ether, ethylene glycol dimethyl ether, diethylene glycol dimethylether and the like. Dimethyl sulfoxide, although an aprotic solvent, is not a suitable solvent since it reacts with the phosphite esters.

As employed herein, the term "lower alkyl" designates alkyl radicals which have from 1 to 4 carbon atoms in a straight or branched chain, for example, methyl, ethyl, propyl, isopropyl, butyl, isobutyl, sec-butyl, and t-butyl.

The term "halo" or "halogen" as employed herein means chlorine, bromine, iodine, and fluorine.

The term "lower alkoxy" includes groups representative of the term "lower alkyl" in combination with oxygen and includes methoxy, ethoxy, propoxy, butyoxy, mixtures thereof and the like.

Illustrative of the substituted phenyl groups which Ar represents are mono-substituted phenyl wherein the substituent is the ortho, metal, or para position, for example, methylphenyl, butylphenyl, methoxyphenyl, butoxyphenyl, fluorophenyl, chlorophenyl, bromophenyl, iodophenyl and the like, and the di-substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl and the like.

The term "aralower alkyl" includes groups representative of the term "lower alkyl" in combination with phenyl groups and includes benzyl and the like.

The following illustrative, non-limiting examples will serve to further demonstrate to those skilled in the art the process of this invention wherein specific compounds within the scope of this invention can be prepared. In the examples, all parts are parts by weight unless otherwise expressly stated.

EXAMPLE 1

Glycine, N,N'-Methylene-Bis-[N-[(Diphenoxyphosphinyl)Methyl]]-, Dimethyl Ester

A solution of diphenylphosphite (22.2 g, 0.095 mole) in 100 mL of acetonitrile was added to a solution containing N-methylene methylglycinate trimer (10.0 g, 0.03 mole) in 200 mL of acetonitrile at 22° C. The resulting solution was gently refluxed for 6 hours, at which time $^{31}$P NMR indicated the complete consumption of the diphenylphosphite. The solution was then cooled to room temperature and concentrated to dryness using a rotovap. The resulting residue was partitioned between methylene chloride and cold, saturated brine. The methylene chloride layer was separated, dried over MgSO$_4$, filtered, and concentrated to an oil. The crude product was purified by preparative thin layer chromatography (Harrison Research Model 7924 Chromatotron) on silica gel eluting with 60:40 ethyl acetate/cyclohexane. The slower eluting product was identified as glycine, N-[(diphenoxyphosphinyl)methyl]-, methyl ester. The faster eluting product gave a yellow oil, $n_D^{22.4} = 1.5422$, which was identified as glycine, N,N'-methylene-bis-[N-[(diphenoxyphosphinyl)methyl]]-, dimethyl ester, corresponding to a compound of Formula IV wherein Ar is phenyl and Y is methyl. NMR ($^1$H, $^{13}$C, $^{31}$P), TLC, mass spectral, and elemental analysis were all consistent with pure product.

Anal. Calc'd. for C$_{33}$H$_{36}$N$_2$O$_{10}$P$_2$: C, 58.07; H, 5.32; N, 4.10; Found: C, 58.12; H, 5.39; N, 3.96.

EXAMPLE 2

Glycine, N,N'-Methylene-Bis-[N-[(Diphenoxyphosphinyl)Methyl]]-, Diethyl Ester

Diphenylphosphite (5.2 g, 0.022 mole) and N-methylene ethylglycinate trimer (2.8 g, 0.008 mole) were combined in 10 mL of acetonitrile. The resulting solution was stirred at 22° C. for 4 hours, at which time $^{31}P$ NMR indicated the complete consumption of the diphenylphosphite. The solution was then concentrated to dryness using a rotovap. The resulting oil was purified by preparative thin layer chromatography (Harrison Research Model 7924 Chromatotron) on silica gel eluting with 40:60 ethyl acetate/cyclohexane. The slower eluting product was identified as glycine, N-[(diphenoxyphosphinyl)methyl]-, ethyl ester. The faster eluting product gave a colorless oil, $n_D^{22.8} = 1.5539$, which was identified as glycine, N,N'-methylene-bis-[N-[(diphenoxyphosphinyl)methyl]]-, diethyl ester, corresponding to a compound of Formula IV wherein Ar is phenyl and Y is ethyl. NMR ($^1H$, $^{31}P$, $^{13}C$), TLC, mass spectral, and elemental analysis were all consistent with pure product.

Anal. Calc'd. for $C_{35}H_{40}N_2O_{10}P_2$: C, 59.15; H, 5.67; N, 3.94; Found: C, 58.90; H, 5.64; N, 3.64.

EXAMPLE 3

Glycine, N,N'-Methylene-Bis-[N-[(Diphenoxyphosphinyl)Methyl]]-, Bis(Phenylmethyl) Ester Diphenylphosphite (2.6 g, 0.011 mole) and N-methylene phenylmethylglycinate trimer (2.1 g, 0.004 mole) were combined in 10 mL of acetonitrile. The resulting solution was stirred at 22° C. for 8 hours, at which time $^{31}P$ NMR indicated the complete consumption of the diphenylphosphite. The solution was then concentrated to dryness using a rotovap. The resulting oil was purified by preparative thin layer chromaography (Harrison Research Model 7924 Chromatotron) on silica gel eluting with 30:70 ethyl acetate/cyclohexane. The slower eluting product was identified as glycine, N-[(diphenoxyphosphinyl)methyl]-, phenylmethyl ester. The faster eluting product gave a colorless oil, $n_D^{23} = 1.5631$, which was identified as glycine, N,N'-methylene-bis-[N-[(diphenoxyphosphinyl)methyl]]-, bis(phenylmethyl)ester, corresponding to a compound of Formula IV wherein Ar is phenyl and Y is phenylmethyl. NMR ($^1H$, $^{13}C$, $^{31}P$), TLC, mass spectral, and elemental analysis were all consistent with pure product.

Anal. Calc'd. for $C_{45}H_{44}N_2O_{10}P_2$: C, 64.74; H, 5.31; N, 3.35; Found: C, 64.61; H, 5.57; N, 3.30.

Other compounds which may be prepared by similar procedures include, but are not limited to, glycine, N,N'-methylene-bis-{N-[[bis(4-methoxyphenoxy)phosphinyl]methyl]}-, diethyl ester and glycine, N,N'-methylene-bis-{N-[[bis(4-chloro-3-methylphenoxy)-phosphinyl]methyl]}-, diethyl ester.

EXAMPLE 4

The post-emergence herbicidal activity of some of the compounds of this invention was demonstrated by greenhouse testing in the following manner. A good grade of top soil is placed in aluminum pans having holes in the bottom and compacted to a depth of 0.95 to 1.27 cm from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks) each pan, except for the control pans, is removed individually to a spraying chamber and sprayed by means of an atomizer operating at a positive air pressure of approximately 1.46 kg/cm² absolute. The atomizer contains 6 mL of a solution or suspension of the chemical. In that 6 mL is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent, such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded.

The post-emergence herbicidal activity index used in Tables I and II is as follows:

| Plant Response | Index |
| --- | --- |
| less than 25% inhibition | 0 |
| 25 to less than 50% inhibition | 1 |
| 50 to less than 75% inhibition | 2 |
| 75 to 99% inhibition | 3 |
| 100% inhibition (complete kill) | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morning Glory | N - Wheat |
| E - Lambsquarters, Common | O - Rice |
| F - Smartweed, Pennsylvania | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass, Large |

*Established from vegetative propagules.
A "—" in the tables indicates that the particular species was absent in the test.

TABLE I

| Compound of Example No. | WAT | kg/h | Plant Species | | | | | | | | | | |
| --- | --- | --- | --- | --- | --- | --- | --- | --- | --- | --- | --- | --- | --- |
| | | | A | B | C | D | E | F | G | H | I | J | K |
| 1 | 2 | 11.2 | — | 3 | 3 | 2 | 3 | 2 | 2 | 3 | 4 | 3 | 3 |
| | 4 | | — | 3 | 4 | 3 | 4 | 3 | 3 | 4 | 4 | 4 | 4 |
| | 2 | 5.6 | — | 3 | 3 | 3 | 3 | 2 | 2 | 3 | 4 | 3 | 4 |
| | 4 | | — | 3 | 4 | 3 | 4 | 3 | 3 | 4 | 4 | 4 | 4 |

TABLE I-continued

| Compound of Example No. | WAT | kg/h | A | B | C | D | E | F | G | H | I | J | K |
|---|---|---|---|---|---|---|---|---|---|---|---|---|---|
| 2 | 2 | 11.2 | — | 3 | 3 | 1 | 3 | 3 | 1 | 2 | 2 | 1 | 3 |
|   | 4 |      | — | 4 | 3 | 1 | 4 | 3 | 2 | 3 | 3 | 3 | 3 |
|   | 2 | 5.6  | — | 2 | 1 | 1 | 3 | 0 | 1 | 1 | 1 | 1 | 1 |
|   | 4 |      | — | 3 | 2 | 1 | 3 | 0 | 2 | 1 | 3 | 2 | 3 |
| 3 | 2 | 11.2 | — | 3 | 1 | 1 | 3 | 0 | 1 | 3 | 1 | 1 | 2 |
|   | 4 |      | — | 3 | 1 | 1 | 3 | 0 | 2 | 3 | 1 | 1 | 3 |
|   | 2 | 5.6  | — | 2 | 1 | 1 | 2 | 0 | 1 | 1 | 1 | 0 | 2 |
|   | 4 |      | — | 3 | 2 | 1 | 2 | 1 | 2 | 1 | 3 | 1 | 3 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 2 | 5.6 | 3 | 4 | 4 | 3 | 3 | 3 | 2 | 3 | 3 | 4 | 4 | 3 | 3 | 4 | 3 | 4 |
|   | 4 |     | 3 | 4 | 4 | 3 | 3 | 4 | 0 | 3 | 2 | 4 | 4 | 4 | 3 | 4 | 4 | 4 |
|   | 2 | 1.12| 2 | 4 | 2 | 2 | 2 | 3 | 3 | 3 | 2 | 3 | 3 | 3 | 1 | 3 | 3 | 3 |
|   | 4 |     | 2 | 4 | 3 | 2 | 2 | 3 | 3 | 3 | 1 | 3 | 3 | 3 | 2 | 3 | 3 | 3 |
|   | 2 | 0.28| 1 | 1 | 1 | 0 | 2 | 3 | 1 | 2 | 1 | 1 | 3 | 2 | 1 | 2 | 2 | 2 |
|   | 4 |     | 1 | 1 | 1 | 0 | 3 | 3 | 2 | 2 | 1 | 1 | 3 | 2 | 1 | 2 | 2 | 2 |
| 2 | 2 | 5.6 | 2 | 1 | 3 | 1 | 3 | 3 | 3 | 2 | 2 | 4 | 3 | 3 | 3 | 3 | 3 | 4 |
|   | 4 |     | 2 | 2 | 4 | 3 | 3 | 3 | 3 | 2 | 2 | 4 | 3 | 3 | 3 | 3 | 3 | 4 |
|   | 2 | 1.12| 1 | 0 | 1 | 1 | 2 | 2 | 2 | 2 | 1 | 3 | 2 | 1 | 2 | 1 | 2 | 3 |
|   | 4 |     | 1 | 0 | 1 | 1 | 2 | 2 | 1 | 1 | 2 | 3 | 2 | 0 | 1 | 2 | 2 | 3 |
|   | 2 | 0.28| 0 | 0 | 0 | 0 | 1 | 0 | 1 | 0 | 0 | 3 | 1 | 0 | 1 | 2 | 1 | 3 |
|   | 4 |     | 0 | 0 | 0 | 1 | 1 | 1 | 1 | 0 | 0 | 3 | 1 | 0 | 1 | 2 | 1 | 3 |
| 3 | 2 | 5.6 | 1 | 2 | 2 | 1 | 3 | 3 | 3 | 2 | 2 | 4 | 3 | 3 | 3 | 3 | 3 | 3 |
|   | 4 |     | 1 | 3 | 3 | 2 | 4 | 3 | 3 | 3 | 3 | 4 | 3 | 3 | 3 | 3 | 4 | 4 |
|   | 2 | 1.12| 1 | 1 | 0 | 1 | 1 | 2 | 1 | 1 | 1 | 3 | 2 | 0 | 1 | 1 | 2 | 3 |
|   | 4 |     | 1 | 2 | 1 | 2 | 2 | 2 | 1 | 2 | 1 | 3 | 2 | 0 | 1 | 2 | 2 | 3 |
|   | 2 | 0.28| 0 | 0 | 0 | 0 | 0 | 0 | 1 | 1 | 0 | 3 | 2 | 0 | 1 | 1 | 1 | 2 |
|   | 4 |     | 0 | 1 | 0 | 0 | 1 | 0 | 0 | 0 | 0 | 3 | 2 | 0 | 1 | 1 | 0 | 2 |

From the test results presented in Tables I and II, it can be seen that the post-emergent herbicidal activity of the compounds of this invention is general in nature. In this regard it should be recognized that each individual species selected for the above tests is a representative member of a recognized family of plant species.

Typically, herbicidal compounds of this invention are provided in the form of concentrates which require dilution prior to application to plants. The usual means for diluting the herbicide is the preparation of herbicidal compositions wherein the compound possessing herbicidal activity is mixed with other materials. Such other materials may be in either liquid or solid form and comprise adjuvants, inert materials, etc.

The herbicidal composition containing herbicidal compounds of this invention are prepared in the usual manner by combining them with other materials which are well known in the herbicide art. The following is a description of herbicidal compositions employing the herbicidal compounds of this invention together with known materials and formulations typically utilized in the herbicide art.

The herbicidal compositions, including concentrates which require dilution prior to application to the plants, of this invention contain from 5 to 95 parts by weight of at least 1 compound of this invention and from 5 to 95 parts by weight of an adjuvant in liquid or solid form, for example, from about 0.25 to 25 parts by weight of wetting agent, from about 0.25 to 25 parts by weight of a dispersant, and, from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least 1 compound of this invention, together with the adjuvants. Where required, from about 0.1 to 2.0 parts by weight of the inert liquid extender can be replaced by a corrosion inhibitor, such as ethanol mercaptan, sodium thiosulfate, dodecylmono or dimercaptan, or antifoaming agent, such as a dimethylpolysiloxane or both. The compositions are prepared by admixing the active ingredient with an adjuvant including diluents, extenders, carriers, and conditioning agents to provide compositions in the form of finely-divided particulate solids, pellets, solutions, dispersions, or emulsions. Thus, the active ingredient can be used with an adjuvant, such as a finely-divided solid, a liquid of organic origin, water, a wetting agent, a dispersing agent, an emulsifying agent, or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, polyoxyethylene derivatives of phenols and alkylphenols (particularly isooctylphenol and nonylphenol), and polyoxyethylene derivatives of the mono-higher fatty acid esters of hexitol anhydrides (e.g., sorbitan). Preferred dispersants are methyl cellulose, polyvinyl alcohol, sodium lignosulfonates, polymeric alkyl naphthalene sulfonates, sodium naphthalene sulfonate, polymethylene bisnaphthalenesulfonate, and sodium N-methyl-N-(long chain acid)-laurates.

When operating in accordance with the present invention, effective amounts of the compounds or compositions of this invention are applied to the plants or are incorporated into aquatic media in any convenient fashion. The application of liquid and particulate solid compositions to plants or soil can be carried out by conventional methods, e.g., power dusters, boom and hand sprayers, and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors, as the plant species and stage of development thereof, and the amount of rainfall as well as the specific compound employed. In foliar treatment for the control of vegetative growth, the active ingredients are applied in amounts from about 0.112 to about 56.0 or more kilograms per hectare. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an adsorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof, and the like. These forms may be assembled in any manner desired including a pipe rock wick, a wedge rope wick, a multi-rope wick, and the like.

In another possible application method, liquid compositions may be selectively applied to weeds by the use of recirculating sprayer systems wherein the recirculating spray unit is mounted on a tractor or high clearance mobile equipment, and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in "Innovative Methods of Post-Emergence Weed Control", McWhorter, C. G., Southern Weed Science Society, 33rd Annual Meeting Proceedings, Jan. 15–17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator—Tool With A Future", Dale, James E., pp. 3–4; "The Recirculating Sprayer and Roundup ® Herbicide", Derting, Claude W., pp. 5–7; and "C.D.A. Herbicide Application", McGarvey, Frank X., *Weeds Today*, Volume 11, Number 2, pp. 8–9, Late Spring, 1980, 309 W. Clark St., Champaign, Ill., U.S.A., the teachings of which are incorporated herein by reference in their entirety.

Although this invention has been described with respect to specific modifications, the details thereof are not to be construed as limitations for it will be apparent that various equivalents, changes, and modifications may be resorted to without departing from the spirit and scope thereof, and it is understood that such equivalent embodiments are intended to be included herein.

What is claimed is:

1. A method of controlling undesired plants which comprises applying to said plants a herbicidally effective amount of a compound of the formula $$(ArO)_2-\overset{O}{\overset{\|}{P}}CH_2NCH_2\overset{O}{\overset{\|}{C}}OY \atop \underset{(ArO)_2-\overset{O}{\overset{\|}{P}}CH_2NCH_2\overset{O}{\overset{\|}{C}}OY}{\overset{CH_2}{|}} \quad (IV)$$

wherein
Ar is a member of the group consisting of phenyl or phenyl substituted with 1 or 2 groups independently selected from the class consisting of halogen, lower alkyl, and lower alkoxy; and
Y is lower alkyl or aralower alkyl.

2. A method of claim 1 wherein Ar is phenyl and Y is lower alkyl.

3. A method of claim 2 wherein said compound is glycine, N,N'-methylene-bis-[N-[(diphenoxyphosphinyl)methyl]]-, dimethyl ester.

4. A method of claim 2 wherein said compound is glycine, N,N'-methylene-bis-[N-[(diphenoxyphosphinyl)methyl]]-, diethyl ester.

5. A method of claim 1 wherein said compound is glycine, N,N'-methylene-bis-[N-[(diphenoxyphosphinyl)methyl]]- bis(phenylmethyl) ester.

6. A compound represented by the formula $$(ArO)_2-\overset{O}{\overset{\|}{P}}CH_2NCH_2\overset{O}{\overset{\|}{C}}OY \atop \underset{(ArO)_2-\overset{O}{\overset{\|}{P}}CH_2NCH_2\overset{O}{\overset{\|}{C}}OY}{\overset{CH_2}{|}} \quad (IV)$$

wherein

Ar is a member of the group consisting of phenyl or phenyl substituted with 1 or 2 groups independently selected from the class consisting of halogen, lower alkyl, and lower alkoxy; and Y is lower alkyl or aralower alkyl.

7. A compound of claim 6 wherein Ar is phenyl and Y is lower alkyl.

8. A compound of claim 7 wherein said compound is glycine, N,N'-methylene-bis-[N-[(diphenoxyphosphinyl)methyl]]-, dimethyl ester.

9. A compound of claim 7 wherein said compound is glycine, N,N'-methylene-bis[N-[(diphenoxyphosphinyl)methyl]]-, diethyl ester.

10. A compound of claim 6 wherein said compound is glycine, N,N'-methylene-bis-[N-[(diphenoxyphosphinyl)methyl]]-, bis(phenylmethyl) ester.

11. A herbicidal composition comprising an adjuvant and a herbicidally effective amount of a compound represented by the formula

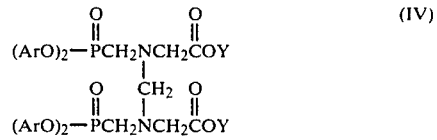

wherein

Ar is a member of the group consisting of phenyl or phenyl substituted with 1 or 2 groups independently selected from the class consisting of halogen, lower alkyl, and lower alkoxy; and Y is lower alkyl or aralower alkyl.

12. A composition of claim 6 wherein Ar is phenyl and Y is lower alkyl.

13. A composition of claim 7 wherein said compound is glycine, N,N'-methylene-bis-[(diphenoxyphosphinyl)-methyl]-, dimethyl ester.

14. A composition of claim 7 wherein said compound is glycine, N,N'-methylene-bis-[N-[(diphenoxyphosphinyl)methyl]]-, diethyl ester.

15. A composition of claim 6 wherein said compound is glycine, N,N'-methylene-bis-[N-(diphenoxyphosphinyl)methyl]]-, bis(phenylmethyl) ester.

* * * * *